US011185222B2

(12) United States Patent
Guevara-Torres et al.

(10) Patent No.: US 11,185,222 B2
(45) Date of Patent: Nov. 30, 2021

(54) LABEL-FREE CONTRAST ENHANCEMENT FOR TRANSLUCENT CELL IMAGING BY PURPOSEFULLY DISPLACING THE DETECTOR

(71) Applicants: Raul Andres Guevara-Torres, Rochester, NY (US); Jesse Schallek, Rush, NY (US)

(72) Inventors: Raul Andres Guevara-Torres, Rochester, NY (US); Jesse Schallek, Rush, NY (US)

(73) Assignee: University of Rochester, Rochester, NY (US)

( * ) Notice: Subject to any disclaimer, the term of this patent is extended or adjusted under 35 U.S.C. 154(b) by 136 days.

(21) Appl. No.: 16/205,925

(22) Filed: Nov. 30, 2018

(65) Prior Publication Data

US 2019/0167094 A1 Jun. 6, 2019

Related U.S. Application Data

(60) Provisional application No. 62/593,471, filed on Dec. 1, 2017.

(51) Int. Cl.
*A61B 3/14* (2006.01)
*A61B 3/10* (2006.01)
*A61B 3/12* (2006.01)

(52) U.S. Cl.
CPC .............. *A61B 3/1025* (2013.01); *A61B 3/12* (2013.01); *A61B 3/1241* (2013.01); *A61B 3/14* (2013.01); *A61B 2503/40* (2013.01)

(58) Field of Classification Search
CPC ........... A61B 3/12; A61B 3/14; A61B 3/1025; A61B 3/0025; A61B 3/1241; A61B 5/14555
USPC ....................................................... 351/206
See application file for complete search history.

(56) References Cited

PUBLICATIONS

Y. N. Sulai et al., "Visualization of retinal vascular structure and perfusion with a nonconfocal adaptive optics scanning light ophthalmoscope", Mar. 2014, J. Opt. Soc. Am. A, vol. 31, pp. 569-579 (Year: 2014).*
A. Guevara-Torres et al., "Imaging translucent cell bodies in the living mouse retina without contrast agents", May 2015, Biomedical Optics Express, vol. 6, pp. 2106-2119 (Year: 2015).*
Artal, P., et al., "Odd aberrations and double-pass measurements of retinal image quality," 1995, J. Opt. Soc. Am. A, vol. 12, No. 2 (pp. 195-201).
Chui, T.Y.P., et al., "The use of forward scatter to improve retinal vascular imaging with an adaptive optics scanning laser ophthalmoscope," 2012, Biomedical Optics Express, vol. 3, No. 10 (pp. 2537-2549).

(Continued)

*Primary Examiner* — Mahidere S Sahle
(74) *Attorney, Agent, or Firm* — Harris Beach PLLC

(57) ABSTRACT

A method for imaging vertebrate translucent retinal structures includes: imaging a translucent retinal structure at a first imaging plane in the retina with a light source focused at such first imaging plane, and detecting reflected light with a non-confocal off-axis detector, wherein the detector is axially displaced from a plane conjugate to the first imaging plane to a plane conjugate to a reflective layer deeper in the retina along a path of illumination from the light source.

12 Claims, 3 Drawing Sheets

(56) References Cited

PUBLICATIONS

Elsner, A. E., et al., "Infrared Imaging of Sub-retinal Structures in the Human Ocular Fundus," 1996, Vision Res., vol. 36, No. 1 (pp. 191-205).
Geng, Y., et al., "Adaptive optics retinal imaging in the living mouse eye," 2012, Biomedical Optics Express, vol. 3, No. 4 (pp. 715-734).
Guevara-Torres, A., et al., "Label free measurement of retinal blood cell flux, velocity, hematocrit and capillary width in the living mouse eye," 2016, Biomedical Optics Express, vol. 7, No. 10 (pp. 4228-4249).
Rossi, E.A., et al., "Imaging individual neurons in the retinal ganglion cell layer of the living eye," 2017, PNAS, vol. 114, No. 3 (pp. 586-591).
Santamaria, J., et al., "Determination of the point-spread function of human eyes using a hybrid optical-digital method," 1987, J. Opt. Soc. Am. A, vol. 4, No. 6 (pp. 1109-1114).
Scoles, D., et al., "In Vivo Imaging of Human Cone Photoreceptor Inner Segments," 2014, IOVS, vol. 55, No. 7 (pp. 4244-4251).
Van Blokland, G.J., et al., "Intenstiy and Polarization of Light Scattered at Small Angles From the Human Fovea," 1986, Vision Res., vol. 26, No. 3 (pp. 485-494).

\* cited by examiner

FIG. 1
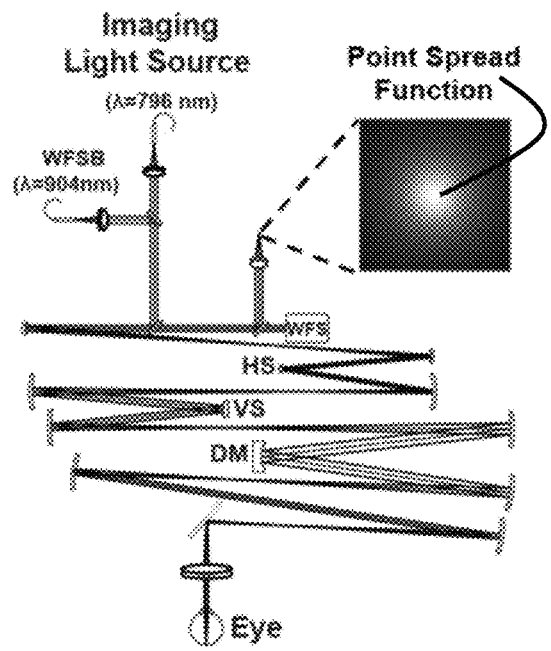
FIG. 2A
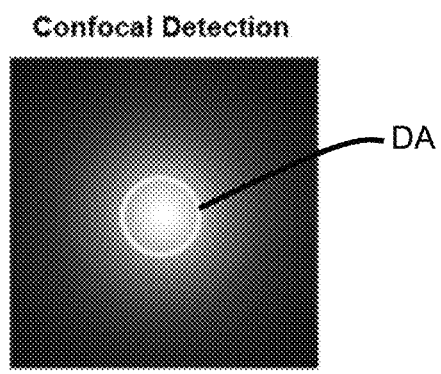
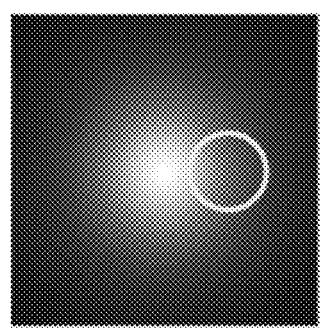
FIG. 2B
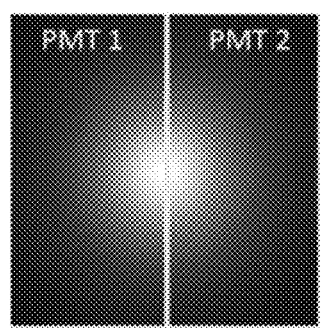
FIG. 2C

Retinal Cell

Reflective Screen

Δx

FIG. 3B  Offset Detection

Detection Aperture

← Left   Right →
*relative to the optical axis

Ganglion Cell Image

Left Edge Bright

Right Illuminated Retinal Cell

Δx

Detection Aperture

Ganglion Cell Image

Right Edge Dark

LABEL-FREE CONTRAST ENHANCEMENT FOR TRANSLUCENT CELL IMAGING BY PURPOSEFULLY DISPLACING THE DETECTOR

CROSS-REFERENCE TO RELATED APPLICATION

This application claims the benefit of U.S. Provisional Application No. 62/593,471, filed Dec. 1, 2017, the disclosure of which is incorporated by reference herein in its entirety.

STATEMENT REGARDING FEDERALLY SPONSORED RESEARCH OR DEVELOPMENT

This invention was made with government support under grant number P30 EY001319 awarded by National Eye Institute. The government has certain rights in the invention.

FIELD OF THE DISCLOSURE

This disclosure relates to the field of retinal imaging, and more particularly to improvements in non-invasive, label-free imaging of translucent retinal cells.

BACKGROUND

The retina is the light sensitive tissue at the back of the eye where the sensation of vision begins. In the vertebrate retina, light must travel through the entirety of retinal neurons before being detected by the photoreceptors. Most of the inner retinal neurons are translucent, providing a benefit for vision but also a formidable challenge to image these cells employing non-invasive microscopic retinal imaging techniques. This lack of cellular contrast in ophthalmic imaging has thus limited basic science and clinical investigation.

Recently, innovations in ophthalmoscopy have sought to optimize resolution and contrast to improve inner retinal cell imaging. To improve resolution, adaptive optics measures and corrects for aberrations of the eye. To improve contrast, non-confocal (off-axis) detection methods have been demonstrated to enhance the phase contrast from translucent retinal cells. Elsner et al. (A. E. Elsner et al., "Infrared imaging of sub-retinal structures in the human ocular fundus," Vision Research 36, 191-205 (1996), e.g., demonstrated that retinal contrast could be improved for some structures when collecting light outside the confocal region in a scanning laser ophthalmoscope by displacing the imaging aperture laterally in the focal plane from the focused illuminated spot ("offset-aperture"). Chui and colleagues (T. Y. P. Chui et al., "The use of forward scatter to improve retinal vascular imaging with an adaptive optics scanning laser ophthalmoscope," Biomed. Opt. Express 3, 2537-2549 (2012)) further applied this principle to the adaptive optics scanning light ophthalmoscope (AOSLO). Sulai and colleagues (Y. N. Sulai et al., "Visualization of retinal vascular structure and perfusion with a nonconfocal adaptive optics scanning light ophthalmoscope," J. Opt. Soc. Am. A 31, 569-579 (2014)) further modified the approach by blocking the confocal light and capturing all of the non-confocal light in two detectors. In this configuration, light to the left of the optical axis in a scanning instrument was collected by one photomultiplier tube (PMT) and light to the right was collected by a second PMT. Sulai found that normalized subtraction of the two images could further remove common information and enhance the asymmetries in the image. Sulai called his method "split-detection" and enabled resolving photoreceptor inner segments (D. H. Scoles et al., "In Vivo Imaging of Human Cone Photoreceptor Inner Segments," IOVS IOVS-14-14542 (2014)).

Using such non-confocal or off-axis detection methods, several groups have demonstrated that a variety of once essentially non-imageable cells can now be visualized in the living retina. Photoreceptor cell bodies and horizontal cells above the monolayer of photoreceptor outer segments, e.g., have been revealed employing offset imaging techniques (A. Guevara-Torres et al., "Imaging translucent cell bodies in the living mouse retina without contrast agents," Biomed. Opt. Express 6, 2106-2119 (2015)). This provided some of the first label-free images of the axial stacking of photoreceptor somas in the living retina. With further optimization, the new capabilities extended to image retinal ganglion cells (E. A. Rossi et al., "Imaging individual neurons in the retinal ganglion cell layer of the living eye," PNAS 114, 586-591 (2017)), which are responsible for transmitting visual information from the eye to the brain.

In addition to neurons, label-free imaging of the retinal vasculature and single blood cells flowing within have been shown (A. Guevara-Torres et al., "Label free measurement of retinal blood cell flux, velocity, hematocrit and capillary width in the living mouse eye," Biomed. Opt. Express, BOE 7, 4228-4249 (2016)). Coupled with fast camera acquisition, the passage of individual red blood cells in capillaries enables new measurements of blood cell flux, hematocrit, velocity in addition to capillary width. This provides new information on the delivery of metabolites in the healthy and diseased retina.

While some inner retinal cells have been successfully imaged employing offset imaging techniques, the source of the contrast has not been completely understood. It would be desirable to provide further understanding of these imaging modalities and provide a method to further optimize contrast for improved non-invasive imaging of such retinal cells.

BRIEF SUMMARY

In accordance with one embodiment of the disclosure, a method for imaging vertebrate translucent retinal structures is described, comprising: imaging a translucent retinal structure at a first imaging plane in the retina with a light source focused at such first imaging plane, and detecting reflected light with a non-confocal off-axis detector, wherein the detector is axially displaced from a plane conjugate to the first imaging plane to a plane conjugate to a reflective layer deeper in the retina along a path of illumination from the light source.

In accordance with one or more various embodiments of such described method, one or more of the following features may be employed alone or in combination: the non-confocal off-axis detector comprises an offset aperture detector or a split detector; the displacement of the detector from a plane conjugate to the first imaging plane to a plane conjugate to a reflective screen layer deeper in the retina increases contrast of a detected retinal structure image; the light source is a laser beam of a scanning light ophthalmoscope; the light source is a laser beam of an adaptive optics scanning light ophthalmoscope; the retinal structure imaged is a ganglion cell; the retinal structure imaged is a horizontal cell; the retinal structure imaged is a photoreceptor; the retinal structure imaged is a bipolar cell; the retinal structure imaged is an amacrine cell; the retinal structure imaged is a blood vessel; the retinal structure imaged is a blood cell; the retinal structure imaged is in the ganglion cell layer; the first imaging plane and retinal structure imaged is positioned between the vitreous and the photoreceptor layer, and wherein the detector is displaced from a plane conjugate to the first imaging plane to a plane conjugate to the photoreceptor layer, or to a plane conjugate to the interface between the choroid and the sclera; the detector is axially displaced from a plane conjugate to the first imaging plane a distance beyond a depth of field of the light source focused at the first imaging plane.

BRIEF DESCRIPTION OF THE SEVERAL VIEWS OF THE DRAWING(S)

FIG. 1 illustrates a system diagram of an AOSLO that may be employed in various disclosed embodiments.

FIGS. 2A-2C illustrate various image detection techniques for the AOSLO of FIG. 1 that may be employed in various disclosed embodiments.

FIGS. 3A-3C and 4A-4C illustrate schematics of described optical model emphasizing the role of cellular refractive index, and ganglion cell images demonstrating observed asymmetric contrast.

DETAILED DESCRIPTION

Figure 3A:
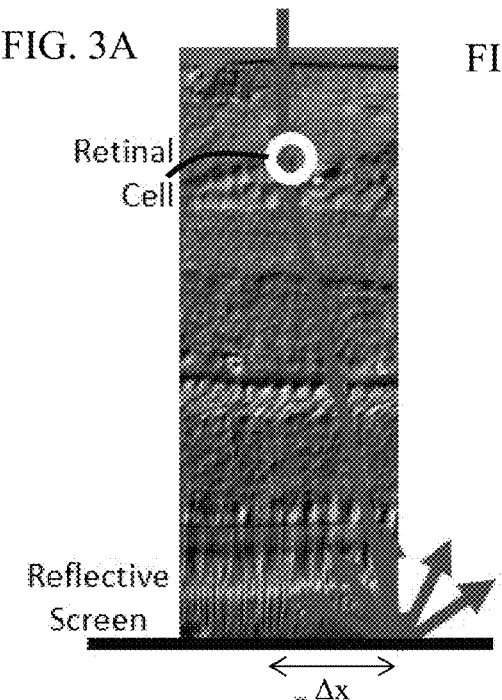
Figure 3A:
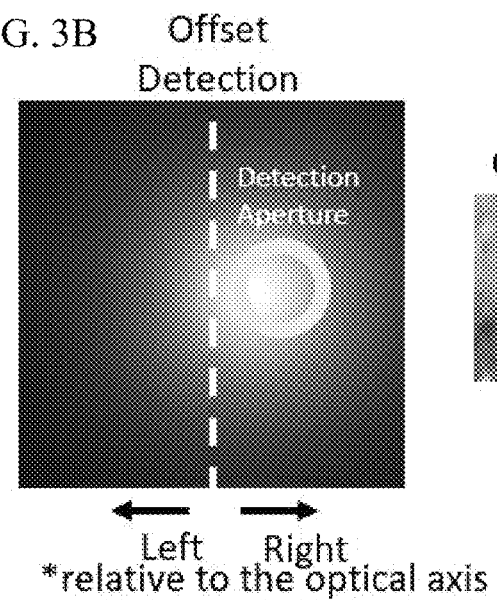
Figure 3C:
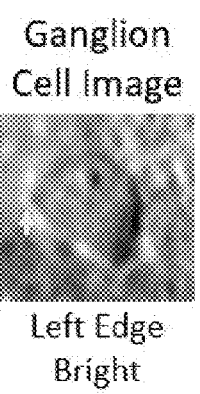

With non-confocal, off-axis detection imaging methods such as offset aperture and split detector techniques, several studies have demonstrated new classes of cells that can be identified using safe-levels of near infrared light. Among the new capabilities provided by these studies are imaging blood vessel wall, individual red blood cells, photoreceptor inner segments, photoreceptor somas, horizontal cells and ganglion cells. Previous models of light scatter provide a partial description of contrast mechanisms. In work by Elsner et al. and further refined by Chui and colleagues referenced above, authors provide a schematic of how light is scattered in offset aperture detection suggesting that light is forward scattered and then reflected by a deeper screen in what they call multiply scattered light. While this model provides an understanding that light interactions in the retina are complex, there is no developed optical model that describes the nature of the asymmetry in the contrast characteristic of offset aperture and split-detection images, complicating further improvements of the techniques.

The present disclosure discloses an optical model of the retina that describes light interaction with the boundaries of these cells, emphasizing the role of refractive index change within the focal plane of illumination. In a simplified model, single cells illuminated by an AOSLO beam act as microscopic spherical lenses which steer the beam to the left or right depending on the polarity of the refractive index change. This not only provides a working model of the asymmetry observed in offset aperture and split-detection images, but it also enables improving the contrast and signal to noise ratio of the collected images by further improving the detector configuration to increase the contrast.

An improved approach to visualize transparent cells that does not require fluorescence and only uses light reflected by the retina is accordingly described. Wavelengths in the visible light spectrum and/or the near infrared spectrum may be employed, as is conventional in optical imaging. The approach emphasizes the role of cellular refractive index change within the plane of illumination to provide an explanation for the origin of the asymmetric contrast in offset aperture and split-detection images, and methods for further optimizing the contrast based on such model are described. More particularly, while it is known that the detector should be placed axially in the same plane as the illumination in confocal systems, the present disclosure describes methods wherein the detector is purposefully "misaligned" in a particular axial direction to provide an enhancement in the contrast and signal to noise ratio in a non-confocal, off-axis detection imaging method.

To demonstrate applicability of the described optical model in providing an improved method for imaging retinal cells, an AOSLO especially designed to image the living mouse retina as described in Y. Geng et. al., "Adaptive optics retinal imaging in the living mouse eye," Biomed. Opt. Express 3, 715-734 (2012), such as illustrated in FIG. 1, may be employed. In brief, the aberrations of the eye are measured in such apparatus using a Shack-Hartmann wavefront sensor (WFS) using 904 nm light as a wavefront sensing beacon (WFSB). The system corrects the aberrations of the eye using a membrane based deformable mirror (DM). The AOSLO is composed of five afocal telescopes that relay the entrance pupil into horizontal (HS) and vertical (VS) scanners, the deformable mirror DM and finally the pupil of the eye. These ophthalmoscopes are scanning instruments, meaning that only one spot is illuminated at a time. The imaging spot is generated with a 796 nm superluminescent diode and it moves in a raster scan pattern using a horizontal fast scanner at 15 kHz and a vertical scanner at 25 Hz. This spot is reimaged into the detector section of the ophthalmoscope, and this light distribution is called the point spread function (PSF) (FIG. 1).

A variety of confocal and non-confocal, off-axis methods have been developed by selecting different subsets of the PSF, such as confocal detection, offset aperture, and split-detection (FIGS. 2A-2C, respectively). For many years, confocal mode has been achieved by placing a circular detection aperture (DA) at the center of the PSF as illustrated in FIG. 2A, maximizing the collection efficiency while enhancing axial sectioning by rejecting out of focus light. It is known that in such confocal systems, the detector should be placed axially in the same plane as the illumination. The offset aperture method is performed by displacing the aperture laterally from the center of the PSF as illustrated in FIG. 2B, and split-detection is performed by separately detecting the left and right portions of the PSF as illustrated in FIG. 2C (e.g., employing photo multiplier tubes PMT1 and PMT2) and then calculating the normalized difference between the two channels.

Although these benefits can be easily transferred to human imaging, the mouse eye may be chosen to advantageously demonstrate the described optical model because it has a large numerical aperture of 0.49 providing optical sectioning in the plane of illumination. The axial resolution improves as the square of the numerical aperture and in the mouse, the numerical aperture is twice as large as that of the human, making the depth of focus four times better in the mouse eye and improving the capabilities to distinguish layers of individual cells. To mitigate the biological variability, every experiment should be repeated in a plurality of mice.

Figure 4A:
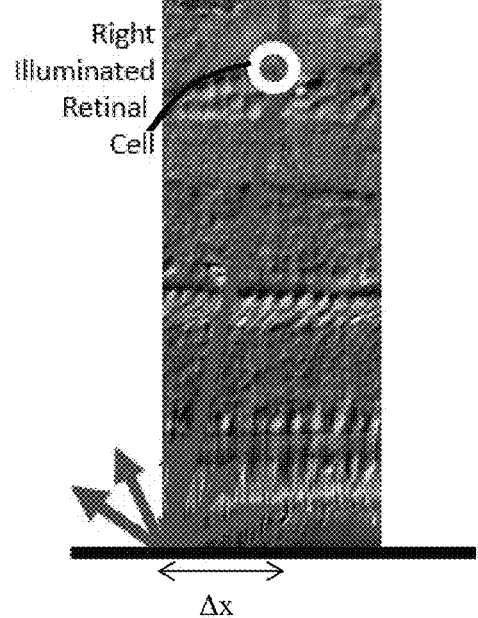
Figure 4B:
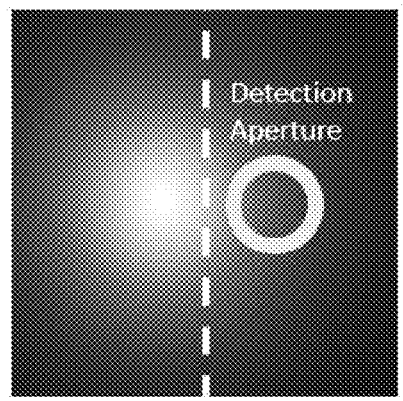
Figure 4C:
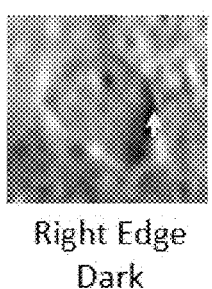

Optical Model: Forward Beam Deviations Due to Changes in Refractive Index Coupled with Deeper Backscattering Layers The present described model considers three steps of light interaction in the retina that are important for providing cell contrast and asymmetry. A simple way to understand this optical model is to consider a cell as though it were a microscopic spherical lens. The aberration corrected spot in an AOSLO is smaller than the average size of the cell found in the retina. When this spot illuminates either the right or left portions of a retinal cell (depicted as the white circle in FIGS. 3A and 4A) as schematically shown in FIGS. 3A-3C and 4A-4C, respectively, the focused beam will be deviated into opposite directions. This beam deviation will be propagated into deeper reflective layers in the retina creating a light distribution that is displaced from the optical axis by a distance Δx as shown in FIGS. 3A and 4A. This displacement will be re-imaged into the detector plane by the AOSLO maintaining the deviation from the optical axis as shown in FIGS. 3B and 4B. With a non-confocal, off-axis detection scheme decentered relative to the optical axis like offset aperture and split-detection, light in one detector will increase when imaging one edge of the cell relative to the other providing asymmetric contrast as shown for ganglion cell images in FIGS. 3C and 4C obtained by split-detection imaging. By coupling with an offset detection aperture in the same direction as the beam deviation, e.g., this will provide a bright pixel in the left edge (FIGS. 3A-3C), while when the offset detection aperture is in the opposite direction as the beam deviation, less light will be coupled through the aperture, providing a dark pixel in the right edge (FIGS. 4A-4C).

Figure 5:
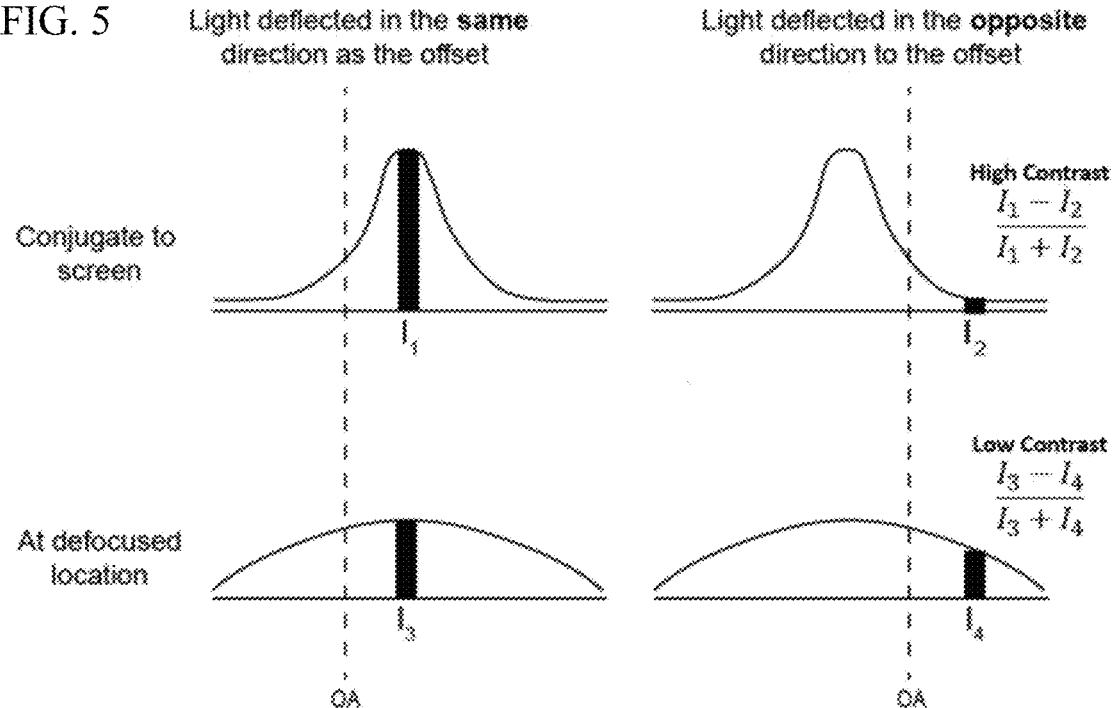
FIG. 5 illustrates a schematic diagram showing light intensities relative to distance from optical axis and the rationale for an increase in the contrast when a detector is axially located at a position conjugate to a detection screen.

This model suggests that when only one edge of the cell is illuminated as the imaging beam is scanned, light is deviated away from the optical axis (OA). As shown in FIG. 5, when this deviation is coupled with an offset detector in the same direction, this will yield a high detected intensity $I_1$ when the detector is conjugate to the screen (i.e., a bright pixel), while when light is deviated in the opposite direction, less light couples through the offset aperture, as the light distribution is highly peaked, and a low intensity $I_2$ is obtained. The difference in intensities relative to the sum will thus provide relatively high contrast in the final images. As the reflection from the screen is assumed to be diffusive, defocus will be added when the offset detector is at any other plane, broadening the decentered light distribution and the difference in intensities $1_3$ and $I_4$ will be smaller relative to the sum further diminishing the contrast. The same analysis can be applied to split-detection or other off-axis detection schemes decentered from the optical axis.

Experiments Testing Optical Model

An AOSLO as described above was used in an offset detection configuration for imaging retinal cells in the mouse eye using aperture diameters between 8 and 40 Airy Disk Diameters (ADD) and displacements between 10 and 50 ADD. The detector aperture is attached to the PMT and move in a three-dimensional stage. The first step is moving the detector axially to the position beyond photoreceptors and this may yield a local maximum in the contrast. In a second step, the plane of illumination is moved to the detector plane that maximizes contrast and this may reveal the mosaic of photoreceptors.

Figure 6:
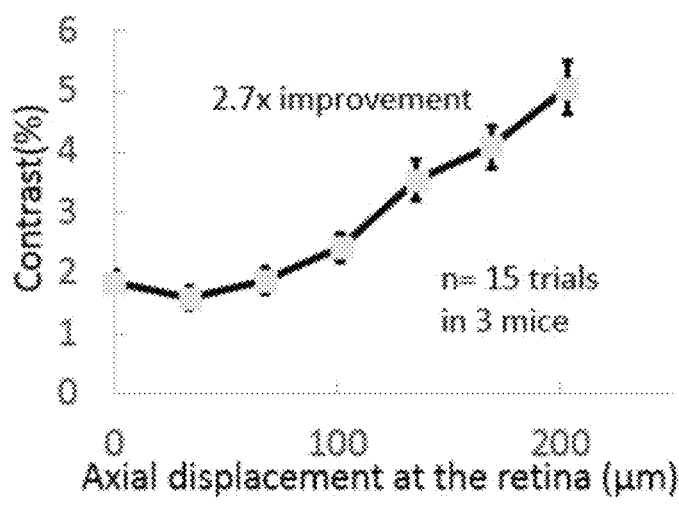
FIG. 6 illustrates data collected in the mouse eye showing a 2.7-fold increase in the contrast when the detector is displaced axially towards the photoreceptors.
Figure 6:
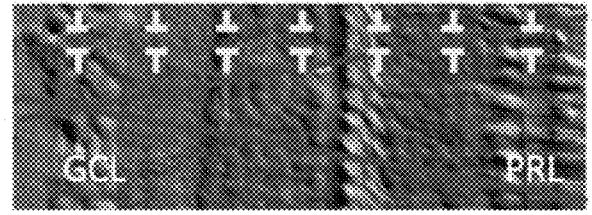

The obtained data as shown in FIG. 6 shows an enhancement in the contrast when the detector is axially displaced from a plane conjugate to the imaged cell layer (ganglion cell layer GCL) a distance beyond a depth of field of the light source focused at the imaged cell layer towards a plane conjugate to a deeper reflective screen (photoreceptor layer PRL). In these experiments, vessels in the ganglion cell layer (GCL) were imaged, and an axial displacement of the detector reached a location close to conjugate to the photoreceptors (PRL). A 60% increase in the collected efficiency and a 2.7-fold increase in the contrast was observed when performing the axial displacement in the detector while imaging these vessels. This example demonstrates that by displacing the detector axially to a position conjugate to a layer of known strong retinal reflection, like the photoreceptor layer, the image contrast will increase.

Strong reflections may be observed from multiple retinal layers. Despite this, a local maximum in the image contrast is expected when the axial displacement is close to the strong reflection of the photoreceptors, or to a plane conjugate to the interface between the choroid and the sclera. In this model, the retinal reflections are assumed to be diffusive. Van Blokland and Van Norren (G. J. Van Blokland et al., "Intensity and polarization of light scattered at small angles from the human fovea," Vision Research 26, 485-494 (1986)) observed two components of the retinal reflection, a wide angle scattered component and a directional one. Even if the two components are present, an improvement from the wide-angle scatter component is still expected to be obtained, and in fact the data shows such an improvement in the contrast and collection efficiency with an axial displacement towards the photoreceptors. The diffuse assumption is also consistent with the double pass-incoherent image based methods to measure ocular aberrations (P. Artal et al., "Odd aberrations and double-pass measurements of retinal image quality," Journal of the Optical Society of America A 12, 195 (1995); J. Santamaria et al., "Determination of the point-spread function of human eyes using a hybrid optical-digital method," Journal of the Optical Society of America A 4, 1109 (1987)).

The present disclosure enables improvements in increasing cell contrast in label-free imaging of a variety of cells that would otherwise be transparent. The described approaches to improving observed contrast for imaged retinal cells can further extend the set of cells that can be distinguished and counted in conditions of health and over the course of retinal disease. While the described optical model and improved method for imaging translucent cells has been specifically demonstrated with respect to AOSLO imaging, this technology has further utility for other forms of microscopy and optical arrangements employing non-confocal, off-axis detection imaging techniques.

The invention claimed is:

1. A method for imaging vertebrate translucent retinal structures comprising:
    imaging a translucent retinal structure at a first imaging plane in the retina with a light source focused at such first imaging plane, and
    detecting reflected light with a non-confocal off-axis detector, wherein the detector is axially displaced from a plane conjugate to the first imaging plane to a plane conjugate to a reflective layer deeper in the retina along a path of illumination from the light source.

2. A method according to claim 1, wherein the non-confocal off-axis detector comprises an offset aperture detector or a split detector.

3. A method according to claim 1, wherein the non-confocal off-axis detector comprises an offset aperture detector.

4. A method according to claim 1, wherein the non-confocal off-axis detector comprises a split detector.

5. A method according to claim 1, wherein the displacement of the detector from a plane conjugate to the first imaging plane to a plane conjugate to a reflective screen layer deeper in the retina increases contrast of a detected retinal structure image.

6. A method according to claim 1, wherein the light source is an imaging beam of a scanning light ophthalmoscope.

7. A method according to claim 1, wherein the light source is an imaging beam of an adaptive optics scanning light ophthalmoscope.

8. A method according to claim 1, wherein the retinal structure imaged is selected from ganglion cells, horizontal cells, photoreceptors, bipolar cells, amacrine cells, blood vessels, and blood cells.

9. A method according to claim 1, wherein the retinal structure imaged is in the ganglion cell layer.

10. A method according to claim 1, wherein the first imaging plane and retinal structure imaged is positioned between the vitreous and the photoreceptor layer, and wherein the detector is displaced from a plane conjugate to the first imaging plane to a plane conjugate to the photoreceptor layer.

11. A method according to claim 1, wherein the first imaging plane and retinal structure imaged is positioned between the vitreous and the photoreceptor layer, and wherein the detector is displaced from a plane conjugate to the first imaging plane to a plane conjugate to the interface between the choroid and the sclera.

12. A method according to claim 1, wherein the detector is axially displaced from a plane conjugate to the first imaging plane a distance beyond a depth of field of the light source focused at the first imaging plane.

\* \* \* \* \*

UNITED STATES PATENT AND TRADEMARK OFFICE
CERTIFICATE OF CORRECTION

PATENT NO. : 11,185,222 B2
APPLICATION NO. : 16/205925
DATED : November 30, 2021
INVENTOR(S) : Raul Andres Guevara-Torres et al.

It is certified that error appears in the above-identified patent and that said Letters Patent is hereby corrected as shown below:

In the Specification

At Column 1, Line number 17, delete:
"This invention was made with government support under grant number P30 EY001319 awarded by National Eye Institute. The Government has certain rights in the invention."

Insert:
--This invention was made with government support under EY001319, and EY028293 awarded by the National Institutes of Health. The government has certain rights in the invention.--

Signed and Sealed this
Tenth Day of December, 2024

Katherine Kelly Vidal
*Director of the United States Patent and Trademark Office*